United States Patent [19]

Ray

[11] Patent Number: 4,637,393
[45] Date of Patent: Jan. 20, 1987

[54] SURGICAL INSTRUMENT

[75] Inventor: Andrew I. A. Ray, Chipperfield, United Kingdom

[73] Assignee: Microsurgical Equipment Limited, United Kingdom

[21] Appl. No.: 623,194

[22] Filed: Jun. 21, 1984

[30] Foreign Application Priority Data

Jun. 21, 1983 [GB] United Kingdom ............... 8316824

[51] Int. Cl.$^4$ ................................................. A61F 17/32
[52] U.S. Cl. .................................................... 128/305
[58] Field of Search ................. 128/305, 305.1, 305.3, 128/310, 311, 774, 653; 73/151.5; 30/272 R, 272 A, 241, 362

[56] References Cited

U.S. PATENT DOCUMENTS 2,591,409 4/1952 Dahl ........................................ 30/241
3,832,776 9/1974 Sawyer ................................. 128/305

OTHER PUBLICATIONS

*Radial Keratotomy*, LAL Publishing, 1980, pp. 201–212, Kremer, M.D., Frederic B., "A New Instrument for Clinical Pachometry".

Primary Examiner—Robert P. Swiatek
Assistant Examiner—Cary E. Stone
Attorney, Agent, or Firm—Diller, Ramik & Wight

[57] ABSTRACT

A surgical instrument in particular for eye surgery has a housing having a good surface for placement on the eye. A knife is held retracted within the housing under the bias of a torsion spring. An ultra-sonic transducer measures the thickness of the part of the eye local to the surface. A control system responds to the measured thickness to displace the knife to project from the surface by an amount related to the depth.

In this way where an incision is effected it can be ensured that the depth of the incision never exceeds the depth of that part of the eye being incised.

8 Claims, 3 Drawing Figures

SURGICAL INSTRUMENT

BACKGROUND OF THE INVENTION

1. Field of the Invention

This invention relates to a surgical instrument for causing a member to penetrate into an organ or body part to a desired depth which is within a desired distance from a remote face of the organ or body part.

2. Description of the Prior Art

Certain processes for example, eye surgery, require that a knife or blade be made to penetrate into the cornea to an accurately controllable depth. In such processes the knife blade, is caused to protrude by a preset amount from a guard resting on the outer surface of the eye ball to be incised.

Great care must be taken not to carry the incision beyond the depth of the cornea since otherwise irreparable damage will result.

Before performing such an operation a surgeon will map out the thickness of the cornea in different places using an ultrasonic tool. Then using the map the surgeon will effect a number of incisions changing the extent of protrusion of the knife between strokes according to the thickness indicated on the map. The process is a highly complex and laborious one and errors are still likely to occur.

It is an aim of the present invention to provide an improved tool for facilitating such processes.

SUMMARY OF THE INVENTION

According to the present invention, there is provided a surgical instrument for causing a member to penetrate into an organ or body part to a desired depth which is within a desired distance from a remote face of the organ or body part, the instrument comprising a said member arranged to be movable by means of drive means with respect to, and so as to extend from, a housing for said member; sensing means for sensing the thickness of the organ or body part in the vicinity of such penetration and arranged to produce a first output signal, said first output signal representing said thickness; setting means for setting said desired depth and arranged to produce a second output signal, said second output signal representing said desired depth; comparator means arranged and connected to compare said output signal and to produce a comparison signal representing any difference between said thickness and said desired depth; and means responsive to said comparison signal to cause, in use of the instrument, said drive means to drive said member to extend from said housing into a said organ or body part to said desired depth.

According to the present invention there is further provided a surgical instrument comprising a housing having a surface for placement on one face of an organ or body part to be worked on, support means for supporting a retractable tool, drive means operable to displace the support means to cause the tool to project from said surface to a desired extent, sensing means for sensing the local thickness of the organ or body part adjacent said surface of the housing and control means for controlling the drive means in a sense to cause the tool to project from the said surface by a desired amount which is a function of the thickness sensed.

BRIEF DESCRIPTION OF THE DRAWINGS

A surgical instrument embodying the invention, will now be described, by way of example only, with reference to the accompanying drawings, in which.

DESCRIPTION OF THE PREFERRED EMBODIMENT

Figure 1:
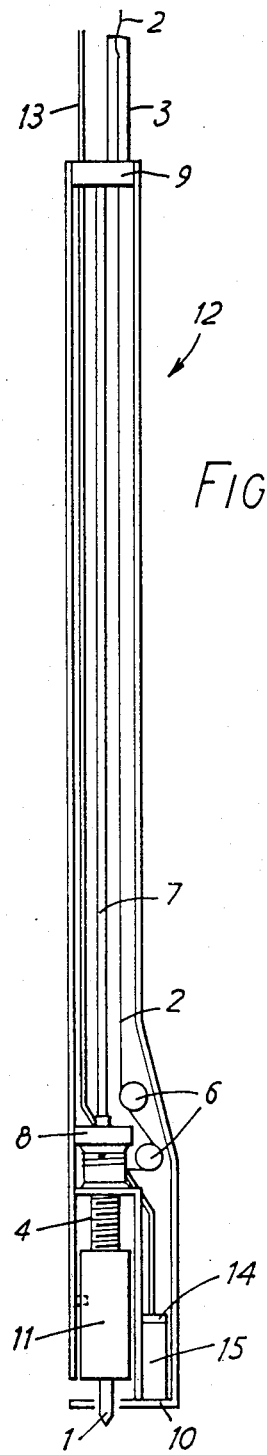
FIG. 1 is a diagrammatic sectional elevation of part of the device.
Figure 3:
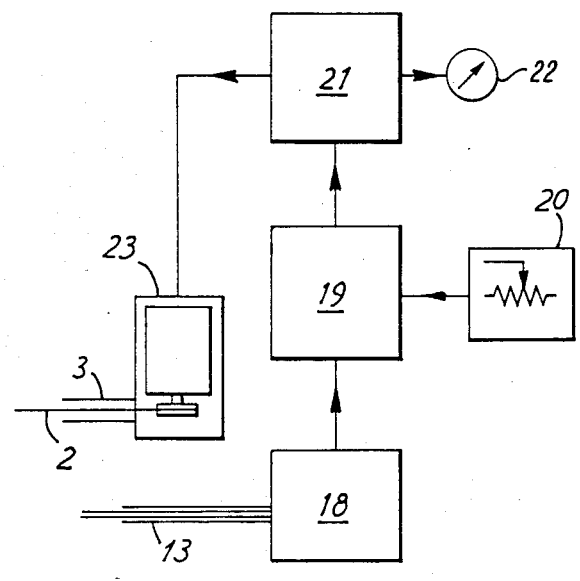
FIG. 3 is a block diagram illustrating the sensing means, setting means, comparator means and means responsive to said comparison signal of the device.
Figure 2:
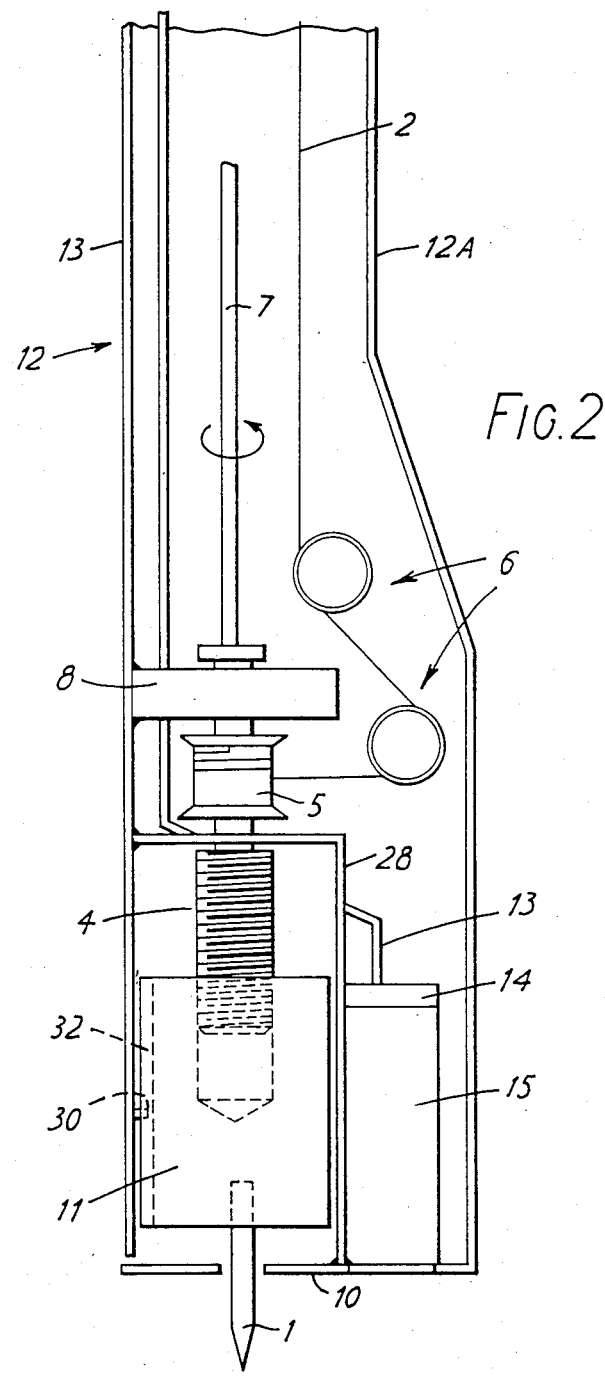
FIG. 2 is fragmentary sectional elevation of part of the device of FIG. 1 to an enlarged scale.

Referring to the drawings, the device comprises a housing 12 supporting a member in the form of a steel or diamond knife 1 which is arranged to be reciprocable by means of drive means with respect to, so as to extend from, a chamber for the knife.

The drive means comprise a cable consisting of a filament or thread 2 tensioned inside a PTFE tube 3; a screw 4, a thread drum 5, a pulley assembly 6 for guiding the thread 2 to the drum 5, a torsion spring 7 for tensioning the thread 2 and retracting the knife 1 in case of thread breakage, bearing blocks 8 and 28 for rotatably supporting the thread drum 5 and a securing block 9 for the torsion spring 7.

The chamber for the knife 1 comprises a knife guard 10 and a slide mounting 11 for the knife 1. The screw 4 which is rigid with the arm 5 screw threadedly engages a screw threaded bore in the mounting 11. A projection 30 rigid with the housing 12 engages a key slot 32 in the mounting 11 to constrain the mounting 11 against rotation about its longitudinal axis.

There is also provided a handle 12A for holding the device, and a thin coaxial cable 13 for electrically connecting the sensing means defined by an ultrasonic transducer to transmitter/receiver element 14, and an ultrasonic coupling piece 15.

The sensing means comprise an ultrasonic transmitter/receiver 18 and an ultrasonic depth measuring circuit 19. The circuit 19 is in the form of a standard ultrasonic depth measuring circuit for measuring propagation times and is well known and understood by those skilled in the art.

The setting means for setting the desired depth comprise a circuit 20 (incorporating a variable resistor) for setting the desired depth which may, if desired, be in the form of a desired percentage of the said thickness.

The aforesaid comparator means are in the form of a servo-amplifier 21 which is also provided with an indicator 22 (for example a voltmeter appropriately calibrated) for displaying the depth of the incision made by the knife 1.

The means responsive to the said comparison signal provided by the servo-amplifier 21 are in the form of a servo-motor and thread winch 23, which cause the drive means hereinbefore described to drive the knife 1 to incise the organ or body part to the desired depth.

In use, the device is energised by an electrical power supply (not shown).

The device illustrated is particularly suitable for ophthalmic surgery, such as for example radial keratotomy procedures, where initially the knife 1 is retracted so as not to protrude from the knife guard 10, and the latter is positioned on the cornea of the eye which is to be incised to the required depth as aforesaid.

It will however be appreciated that, whilst the invention has been specifically described in the context of surgery, the scope of the inventon is not limited to such application, since it can find application also in any operation on any organ or body part into which a tool or other member (e.g. a probe) is to be inserted, or in which a "blind" hole or incision is to be made to an accurately predetermined depth related to a face of the organ or body part remote from the member.

Without prejudice to the generality of the term "member", the latter is intended to include within its scope a surgical tool such as a surgical knife, cutter, blade, drill or the like.

Many modifications can be made to the invention without departing from the spirit and scope of the invention as defined in the appended claims.

I claim:

1. A surgical instrument for causing a member to penetrate into an organ or body part to a depth which is within a desired distance from a remote face of the organ or body part, the instrument comprising
   a said member,
   a housing for housing said member,
   drive means for driving said member with respect to and so as to extend from said housing,
   sensing means mounted on the housing for sensing the thickness of the organ or body part in the vicinity of such penetration and arranged to produce a first output signal, said first output signal representing said thickness,
   setting means settable to a level indicative of said desired distance and arranged to produce a second output signal, said second output signal representing said desired distance,
   comparator means arranged and connected to compare said output signals and to produce a comparison signal representing any difference between said thickness and said desired distance, and
   means responsive to said comparison signal to cause said drive means to drive said member to extend from said housing into a said organ or body part to a depth which is said desired distance from said remote face.

2. An instrument according to claim 1 wherein said member comprises a surgical knife.

3. An instrument according to claim 1 wherein the sensing means comprises
   an ultrasonic transducer capable of transmitting ultrasonic pulses into the organ or body part and receiving an "echo" from said remote face of the organ or body part, and
   means for providing a said first output signal representing the time delay between transmitted and received said pulses, the said time delay being a function of said thickness.

4. A surgical instrument comprising
   a housing having a surface for placement on one face of an organ or body part to be worked on,
   a tool retractable within the housing,
   support means for supporting the retractable tool,
   drive means operable to displace the support means to cause the tool to project from said surface to a desired extent,
   sensing means for sensing the local thickness of the organ or body part adjacent said surface of the housing, and
   control means for controlling the drive means in a sense to cause the tool to project from the said surface by a desired amount which is a function of the thickness sensed,
   biasing means for urging the tool into a retracted position with the housing,
   a drum,
   a screw threaded member rigid with said drum and in screw threaded engagement with the support means,
   means for constraining the support means against rotation,
   a drive, and
   an elongated filament rigid with said drum, partially wrapped around said drum and coupled to said drive whereby when said drive pulls said filament the drum is rotated and said knife is displaced axially of said drum to project from said housing.

5. An instrument according to claim 4 including pulley means for guiding said elongate filament through said housing to said drum.

6. An instrument according to claim 4 wherein said drive comprises a servomotor carrying a winch to which said elongate filament is attached.

7. An instrument according to claim 4 wherein said sensing means comprises an ultra-sonic transducer.

8. An instrument according to claim 7 wherein
   said control system determines desired depths of penetration for every measured thickness and controls the drive means in a sense to cause the tool to project from said surface by an amount equal to the determined desired depth of penetration.

* * * * *